(12) United States Patent
Greff et al.

(10) Patent No.: US 6,646,133 B1
(45) Date of Patent: Nov. 11, 2003

(54) PROCESS FOR THE PREPARATION OF AMORPHOUS ATORVASTATIN CALCIUM

(75) Inventors: Zoltan Greff, Budapest (HU); Peter Kotay Nagy, Vac (HU); Jozsef Barkoczy, Budapest (HU); Gyula Simig, Budapest (HU); Laszlo Balazs, Budapest (HU); Imre Doman, Budapest (HU); Zoltan Ratkai, Budapest (HU); Peter Seres, Budapest (HU); Zsuzsa Szent Kirallyi, Budapest (HU); Ferenc Barta, Tiszavasvari (HU); Gyorgyi Vereczkeyne Donath, Budapest (HU); Kalman Nagy, Budapest (HU)

(73) Assignee: Egis Gyogyszergyar Rt., Budapest (HU)

( * ) Notice: Subject to any disclaimer, the term of this patent is extended or adjusted under 35 U.S.C. 154(b) by 0 days.

(21) Appl. No.: 10/110,874

(22) PCT Filed: Oct. 17, 2000

(86) PCT No.: PCT/HU00/00106

§ 371 (c)(1),
(2), (4) Date: Jul. 3, 2002

(87) PCT Pub. No.: WO01/28999

PCT Pub. Date: Apr. 26, 2001

(51) Int. Cl.$^7$ ............................................ C07D 207/337
(52) U.S. Cl. ....................................................... 548/537
(58) Field of Search ......................................... 548/537

(56) References Cited

U.S. PATENT DOCUMENTS 5,273,995 A   12/1993   Roth

FOREIGN PATENT DOCUMENTS

WO   WO-97/03960   2/1997

*Primary Examiner*—Joseph K. McKane
*Assistant Examiner*—Sonya Wright
(74) *Attorney, Agent, or Firm*—Herbert Dubno

(57) ABSTRACT

The invention relates to a process for the preparation of amorphous atorvastatin calcium by recrystallization of crude atorvastatin from an organic solvent which comprises dissolving crude amorphous atorvastatin calcium in a lower alkanol containing 2–4 carbon atoms or a mixture of such alkanols under heating and isolating the amorphous atorvastatin calcium precipitated after cooling. The atorvastatin calcium obtained is a known valuable agent useful in treating hyperlipidemia and hypercholestrolemia.

4 Claims, 2 Drawing Sheets

US 6,646,133 B1

PROCESS FOR THE PREPARATION OF AMORPHOUS ATORVASTATIN CALCIUM

Figure 1:
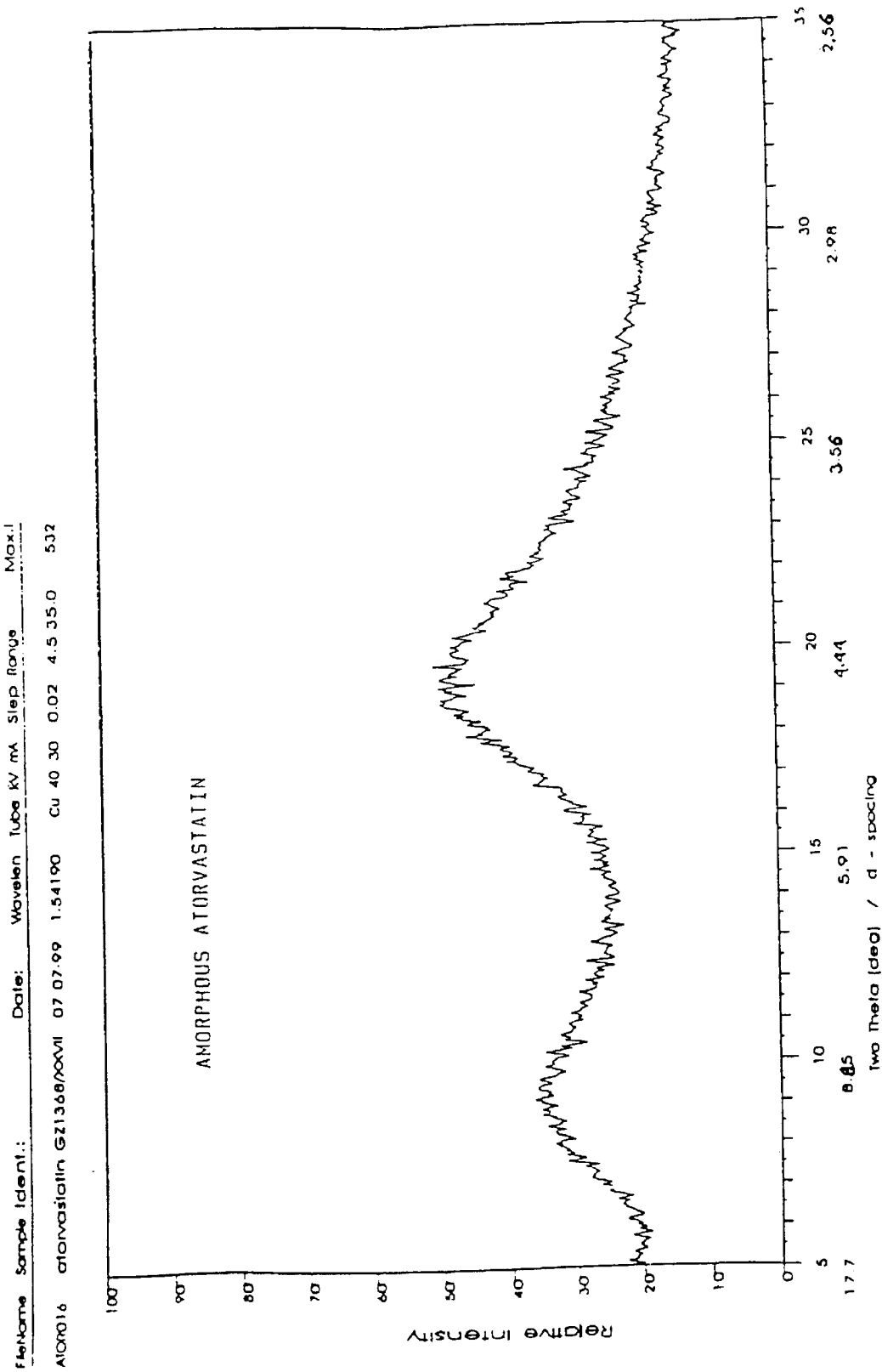

This application is a 371 of PCT/HU00/00106 filed Oct. 17, 2000.

TECHNICAL FIELD

The invention relates to an improved new process for the preparation of atorvastatin calcium.

STATE OF THE ART

The calcium salt of [R-($R^x$,$R^x$)]-2-(4-fluorophenyl)-β,δ-dihydroxy-5-[1-methyl-ethyl)-3-phenyl-4-[(phenylamino)-carbonyl]-1H-pyrrole-1-heptanoic acid having the INN atorvastatin is an inhibitor of the 3-hydroxy-3-methylglutamine coenzyme A reductase enzyme. Due to this effect atorvastatin is a valuable lipide and cholesterol level decreasing agent and useful in treating hyperlipidemia and hypercholesterolemia. Atorvastatin was described the first time in U.S. Pat. No. 5,273,995. In this US patent specification there is no disclosure concerning the crystalline form of the product. The preparation of atorvastatin and key intermediates useful in the synthesis are described at several places in prior art (e.g. U.S. Pat. No. 5,003,080, U.S. Pat. No. 5,097,045, U.S. Pat. No. 5,103,024, U.S. Pat. No. 5,124,482, U.S. Pat. No. 5,149,837, U.S. Pat. No. 5,155,251, U.S. Pat. No. 5,216,174, U.S. Pat. No. 5,245,047, U.S. Pat. No. 5,248,793, U.S. Pat. No. 5,280,126, U.S. Pat. No. 5,397,792 and U.S. Pat. No. 5,342,952).

The preparation of atorvastatin calcium in a defined crystalline form is first described in WO 97/03958.

In prior art four different polymorphs of atorvastatin calcium are disclosed. WO 97/03958 relates to crystalline Form III of atorvastatin calcium. According to this published PCT application crystalline Form III is prepared by allowing to stand atorvastatin calcium containing crystalline Form II under a moisture content of 95% for 11 days.

In WO 97/03959 crystalline Forms I, II and IV of atorvastatin calcium are claimed and disclosed.

According to the examples of this published PCT application crystalline Form I can be prepared in two ways. According to one of the processes the product is obtained by seeding with crystalline Form I. According to the other process a mixture of amorphous and crystalline Form I atorvastatin calcium is stirred in a 17:3 volume/volume mixture of water and methanol at 40° C. for 17 hours.

According to the examples of WO 97/03959 crystalline Form II is prepared by suspending a mixture of amorphous and crystalline Form I atorvastatin calcium in a 20-fold amount of a 3:2 volume mixture of methanol and water and stirring the suspension for 3 days.

Crystalline form IV is prepared from atorvastatin lactone. According to the examples of WO 97/03959 the aqueous mixture obtained in course of the formation of the calcium salt of atorvastatin is heated at 65–70° C. for at least 5 minutes, whereupon the mixture is cooled to 55–65° C. The precipitated crystals are filtered, stirred in methanol at 55–60° C., the suspension is cooled to 25–30° C. and finally the crystalline Form IV is isolated by filtration.

Amorphous atorvastatin shows numerous advantages over the crystalline Form. According to prior art amorphous atorvastatin calcium gives varying dissolution characteristics and in some cases varying bioavailability data are obtained as compared to the crystalline Form [Konno T., Chem. Pharm. Bull., 38, 2003–2007 (1990)]. In some therapeutical indications certain bioavailability characteristics are more preferable than others. For this reason there is a need towards a process which enables the preparation of amorphous atorvastatin calcium.

In WO 97/03960 a new process is disclosed for the preparation of amorphous atorvastatin calcium starting from crystalline Form I. According to the main claim of this published international application crystalline Form I atorvastatin calcium is dissolved in a hydroxy-free solvent, whereupon the solvent is removed to yield amorphous atorvastatin. The sub-claims protect the use of tetrahydrofurane per se or a mixture of tetrahydrofurane and toluene as hydroxy-free solvent. According to the examples crystalline Form I is dissolved in an approximately four-fold amount of a 3:2 mixture of tetrahydrofurane and toluene, whereupon the solvent is removed by special drying technology. Drying is carried out in an apparatus manufactured specially for this purpose at first at 35° C., and thereupon at 85° C., in vacuo at 6–8 Hgmm for 4 days.

The disadvantage of the process disclosed in WO 97/03960 is that amorphous atorvastatin is prepared from a defined crystalline Form, namely from crystalline Form I. The preparation of this polymorph is disclosed in WO 97/03959. According to the teaching of this reference the process is complicated and can be reproduced only with difficulties. On page 20 lines 14–19 the following statement is set forth:

"The precise conditions under which crystalline Form I atorvastatin is formed may be empirically determined and it is only possible to give a number of methods which may be found suitable in practice."

SUMMARY OF THE INVENTION

It is the object of the invention to eliminate the drawbacks of the known procedures and to provide a simple and economically feasible process for the preparation of high purity and uniformly amorphous atorvastatin calcium.

The above object is solved by the following process of the invention.

According to the invention there is provided a process for the preparation of amorphous atorvastatin calcium by recrystallization of crude atorvastatin from an organic solvent which comprises dissolving crude atorvastatin calcium in a lower alkanol containing 2–4 carbon atoms or a mixture of such alkanols under heating and isolating the amorphous atorvastatin calcium precipitated after cooling.

DETAILED DESCRIPTION OF THE INVENTION

It has been surprisingly found that uniformly amorphous atorvastatin calcium can be obtained in a simple and reproducible manner by recrystallizing crude atorvastatin calcium from an alkanol containing 2–4 carbon atoms or a mixture of two or more such alkanols. The above recognition is so much the more surprising as according to the teaching of WO 97/03960 exclusively hydroxy-free solvents are suitable for the preparation of amorphous atorvastatin.

According to the process of the present invention ethanol, n-propanol, isopropanol, n-butanol or branched-chain butanols can be used as alkanol containing 2–4 carbon atoms. It is preferred to use isopropanol or ethanol, or a mixture of isopropanol and ethanol. The process may also be carried out by using a mixture of two or more alkanols.

As starting material one may preferably use crude atorvastatin calcium, a product prepared according to U.S. Pat. No. 5,273,995.

According to a preferred form of realization of the process of the present invention one may proceed as follows:

The starting material is dissolved in an alkanol containing 2–4 carbon atoms under heating, advantageously at the boiling point of the solvent. One may proceed preferably by filtering the solution, allowing the filtrate to cool to room temperature and allowing the suspension to stand in the cold. The precipitated amorphous atorvastatin calcium is isolated by filtration or centrifuging, washed with the cold alkanol containing 2–4 carbon atoms used for recrystallization and finally dried in vacuo. One may also work by filtering the hot solution into boiling $C_{2-4}$ alkanol and then proceeding as described above.

The process of the present invention can be performed in a short period of time. Depending on the amount of the starting material the reaction time amounts to some hours.

The process of the present invention has the following advantages:

- The process provides in a simple and reproducible manner uniformly high purity amorphous product having advantageous properties from the point of view of pharmaceutical industry.
- Amorphous atorvastatin calcium is obtained from crude atorvastatin which can be easily prepared rather than from circumstantially available crystalline Form I.
- The evaporation of the solvent and the circumstantial removal of the traces of solvents are eliminated. The desired product is isolated in a simple manner by filtration of the amorphous product precipitated on cooling the warm solution.
- As a result of the above advantages the process can be carried out in a short time by using simple equipment.
- The process is highly suitable for industrial scale manufacturing.
- The solvents used in the process are not detrimental to the environment.

Further details of the present invention are to be found in the following Examples without limiting the scope of protection to said Examples.

EXAMPLE 1

2.74 g (2.37 millimoles) of crude atorvastatin calcium are according to Example 10 of U.S. Pat. No. 5,273,995 are heated to boiling in 120 ml of 2-propanol until the material goes into solution. The hot solution thus obtained is filtered into 20 ml of boiling 2-propanol and allowed to cool to room temperature. The isopropanol suspension is allowed to stand at 4° C. for 4 hours. The precipitated amorphous product is filtered off, washed with cold isopropanol (4° C.) and dried at 55 Pa in vacuo at room temperature. 2.50 g of uniformly amorphous atorvastatin calcium are obtained. Yield 91.2%.

The X-ray powder diffraction pattern of the product is shown on the enclosed FIG. 1.

Apparatus: PHILIPS—PW 1820 powder diffractometer
Radiation: Cu Kα (λ: 1,54190 Å)
Monochromator: graphite
Exciting voltage: 40 kV
Anode current: 30 mA
Sample: smooth surface, thickness 0,5 mm.

Measurement of the X-ray structure (X-ray diffraction) is based on the diffraction and interference of the electrons of the lattice atoms. The ordered, lattice structure characterizing crystalline materials is displayed by the reflexion (interference maxima) of the X-ray patterns. Owing to their disordered structure, amorphous materials do not display sharp peaks on the diffraction pattern, they are characterized only by flattened curves. With the use of X-ray diffraction one can therefore unambiguously verify the crystalline or amorphous state of a material.

Figure 2:
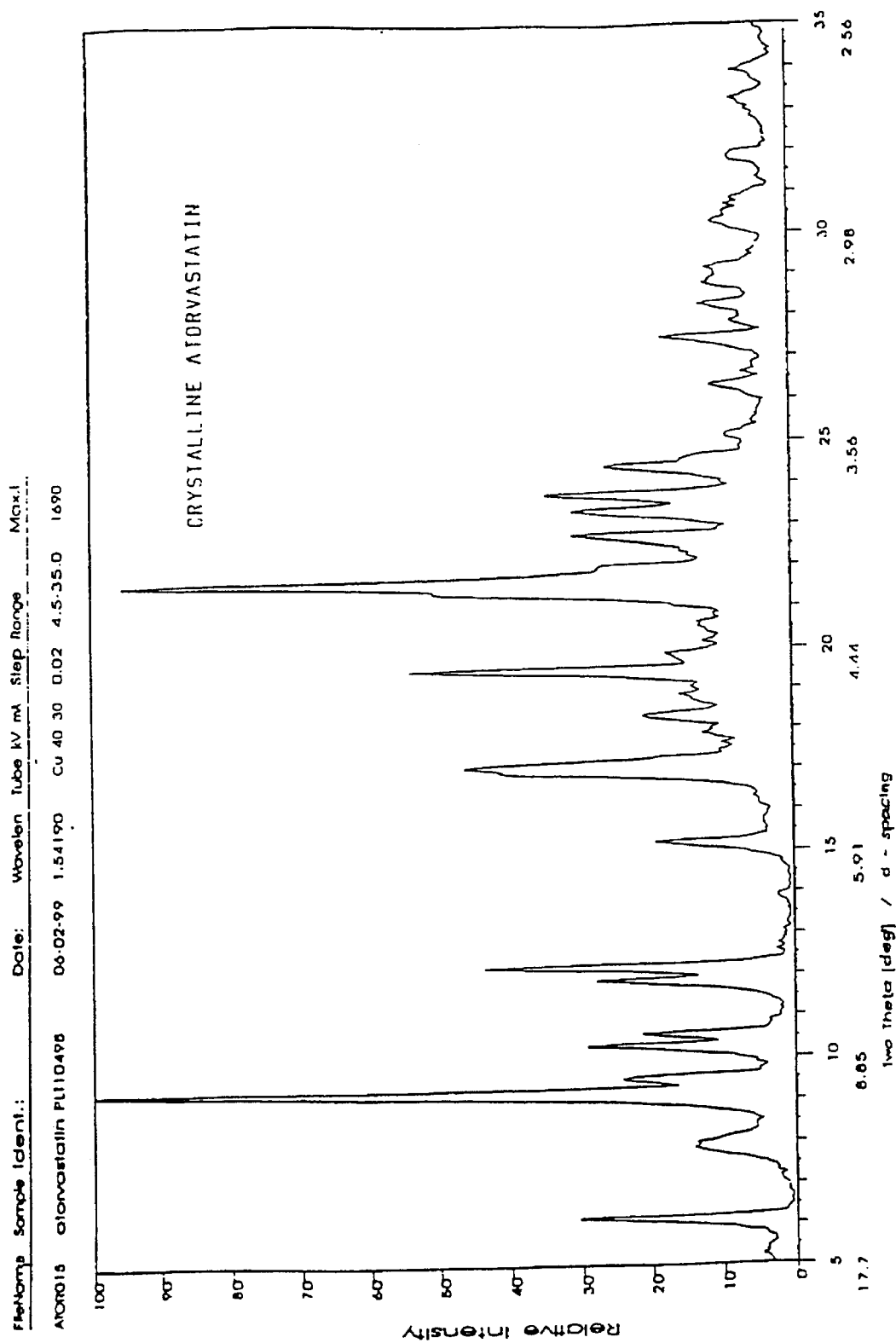

The X-ray powder diffraction pattern of the crystalline atorvastatin is shown on the enclosed FIG. 2.

EXAMPLE 2

2.00 g (1.73 millimoles) of amorphous atorvastatin calcium salt are heated to boiling in 20 cm$^3$ of ethanol until the material goes into solution (approx. 1 minute). The hot solution obtained is filtered into 100 cm$^3$ of boiling 2-propanol and allowed to cool to room temperature, while the precipitation of the amorphous atorvastatin calcium salt begins. The suspension obtained is allowed to stand at 4° C. for 4 hours, then filtered, washed with 5 cm$^3$ of 2-propanol (4° C.) and dried at 55 Pa in vacuo at room temperature. Thus 1.74 g (87%) of amorphous atorvastatin calcium salt are obtained.

We claim:

1. Process for the preparation of amorphous atorvastatin calcium by dissolving crude atorvastatin calcium in an organic solvent, which comprises dissolving crude atorvastatin calcium in a lower alkano containing 2–4 carbon atoms or in a mixture of such alkanols under heating and isolating the amorphous atorvastatin calcium precipitated after cooling.

2. Process according to claim 1 wherein the lower alkanol is isopropanol or ethanol, or a mixture of isopropanol and ethanol as alkanol containing 2–4 carbon atoms.

3. Process according to claim 1 which comprises dissolving the starting material in 2-propanol or in ethanol at the boiling point of the solvent.

4. Process according to claim 1 which comprises cooling the solution and isolating the precipitated amorphous atorvastatin calcium by filtration or centrifuging.

* * * * *